United States Patent [19]

Brown et al.

[11] Patent Number: 5,629,299

[45] Date of Patent: *May 13, 1997

[54] HYDROLYTIC STABILIZER FOR UNSTABLE ORGANIC IONS

[76] Inventors: Nesbitt D. Brown, 5139 Celestial Way, Columbia, Md. 21044; Bhupendra P. Doctor, 10613 Great Arbor Dr., Potomac, Md. 20854; Joseph M. Marasco, 479 Brookside La., Somerville, N.J. 08876

[ * ] Notice: The term of this patent shall not extend beyond the expiration date of Pat. No. 5,238,927.

[21] Appl. No.: 108,290

[22] Filed: Aug. 19, 1993

Related U.S. Application Data

[63] Continuation of Ser. No. 912,569, Jul. 13, 1992, Pat. No. 5,238,927, which is a continuation of Ser. No. 621,654, Nov. 30, 1990, abandoned.

[51] Int. Cl.$^6$ .................. A61K 31/70; A61K 31/44; A01N 43/40
[52] U.S. Cl. .................................. 514/58; 514/277
[58] Field of Search .................. 514/58, 277; 536/103; 604/51

[56] References Cited

U.S. PATENT DOCUMENTS

| | | | |
|---|---|---|---|
| 3,459,731 | 8/1969 | Gramera et al. | 514/58 |
| 4,226,235 | 10/1980 | Sarnoff et al. | 514/58 |
| 4,226,236 | 10/1980 | Genese | 514/58 |
| 4,305,947 | 12/1981 | Bartner | 514/58 |
| 4,394,863 | 7/1983 | Bartner | 514/58 |
| 4,689,042 | 8/1987 | Sarnoff et al. | 514/58 |
| 4,727,064 | 2/1988 | Pitha | 514/58 |
| 4,755,169 | 7/1988 | Sarnoff et al. | 514/58 |
| 4,834,985 | 5/1989 | Elger et al. | 514/58 |
| 4,869,904 | 9/1989 | Uekama et al. | 514/58 |
| 4,983,586 | 1/1991 | Bodor | 514/58 |
| 5,002,935 | 3/1991 | Bodor | 514/58 |
| 5,092,843 | 3/1992 | Monroe et al. | 514/58 |
| 5,238,927 | 8/1993 | Brown et al. | 514/58 |
| 5,324,750 | 6/1994 | Lincoln et al. | 514/58 |

FOREIGN PATENT DOCUMENTS

| | | |
|---|---|---|
| 0335545B1 | 3/1989 | European Pat. Off. . |
| 335545 | 10/1989 | European Pat. Off. . |

OTHER PUBLICATIONS

The Merck Index, an Encyclopedia of Chemicals, Drugs and Biologicals, Tenth Edition, 1983 published by Merch & Co., Inc., Rahway, NJ, USA, p. 1107, item 7601.
Green et al., *J. Pharm. Sci.*, 78(5), 427–31 (May, 1989).
Bekers et al., *Proc. Fourth Int. Sym. on Cyclodextrins* (Huber and Szejtli, Eds.), 313–317 (1988).
Bekers et al., *Pharm. Week*, 10, 207–12 (1988).
Yonezawa et al., *Agric. Biol. Chem.*, 45(2), 505–6 (1981).
Glomot et al., *Int. J. Pharm.*, 46, 49–55 (1988).
*The Merck Index*, Eleventh Edition, Merck & Co., Inc. 1989, p. 318.
El Gezawi et al., *J. Pharm. Biomed. Anal.*, 6(4), 399–406 (1988).
Eyer et al., *Arch. Toxicol.*, 62(2–3), 224–6 (1988).
Duchene et al., *Pharmaceutical Technology*, 22–30 (Aug. 1991).
Szejtli, *Pharmaceutical Technology*, 24–30 (Aug. 1991).

*Primary Examiner*—Gary L. Kunz
*Attorney, Agent, or Firm*—Lerner, David, Littenberg, Krumholz & Mentlik

[57] ABSTRACT

Storage-stable aqueous solutions of hydrolytically unstable organic ionic compounds and cyclodextrins, which cyclodextrins are capable of forming hydrolytically stable inclusion complexes with the ionic compounds. Storage-stable rapidly solvated organic ionic inclusion complexes of hydrolytically unstable organic ionic compounds and cyclodextrins, which cyclodextrins are capable of forming hydrolytically stable inclusion complexes with the ionic compounds. Systems for rapidly administering aqueous solutions effective in the treatment of organophosphorus toxin nerve poisoning to a mammal in need thereof combining a storage-stable aqueous solution of an inclusion complex of a hydrolytically unstable quaternary pyridinium oxime or aldoxime compound capable of reactivating carboxy, choline and esterases inhibited by the organophosphorus toxins and a cyclodextrin capable of forming a hydrolytically stable inclusion complex with the quaternary pyridinium compounds, and means for rapidly administering the aqueous solution. Systems for rapidly administering aqueous solutions effective in the treatment of organophosphorus toxin nerve poisoning combining the inclusion complex with means for rapidly solvating and administering the inclusion complex.

37 Claims, 6 Drawing Sheets

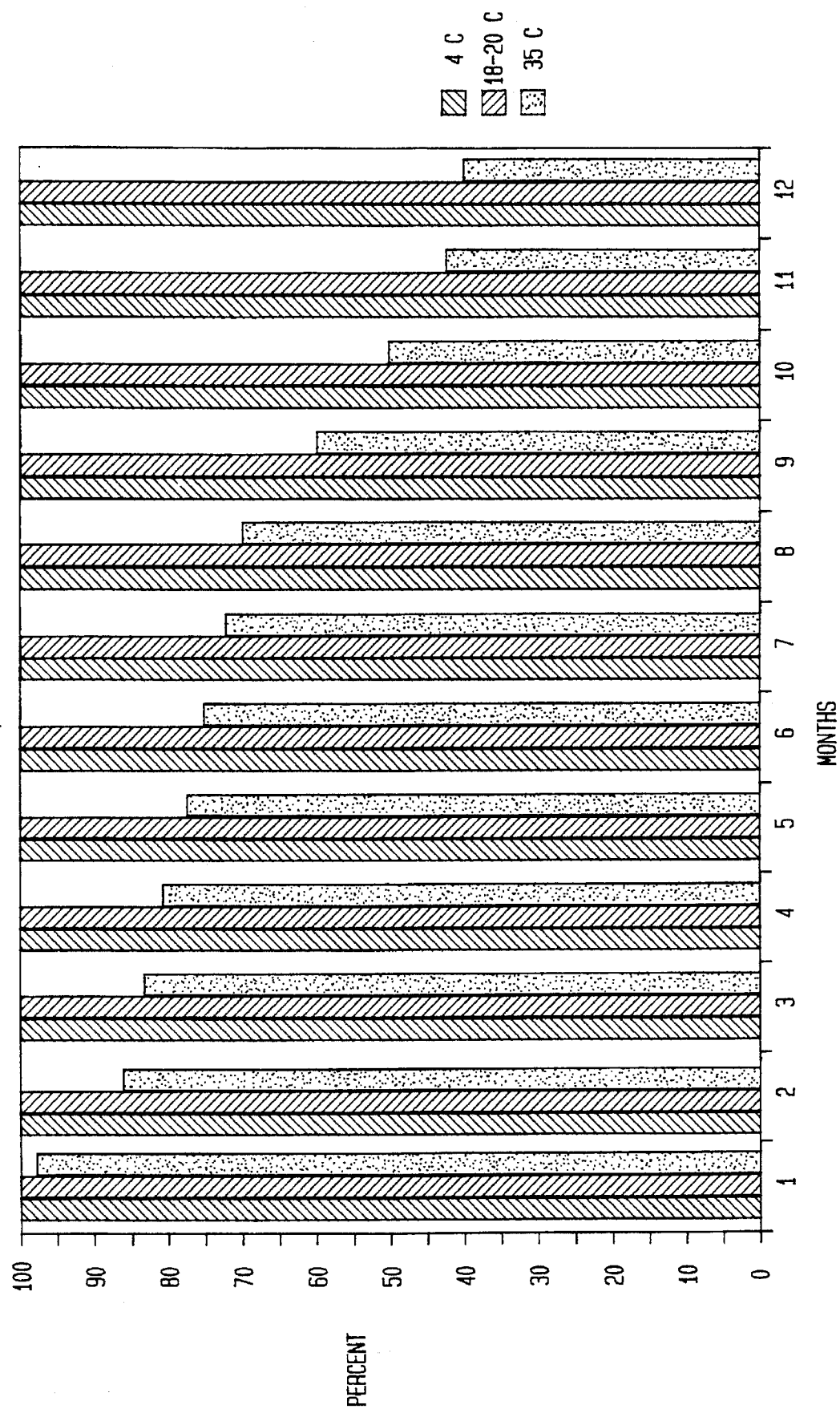

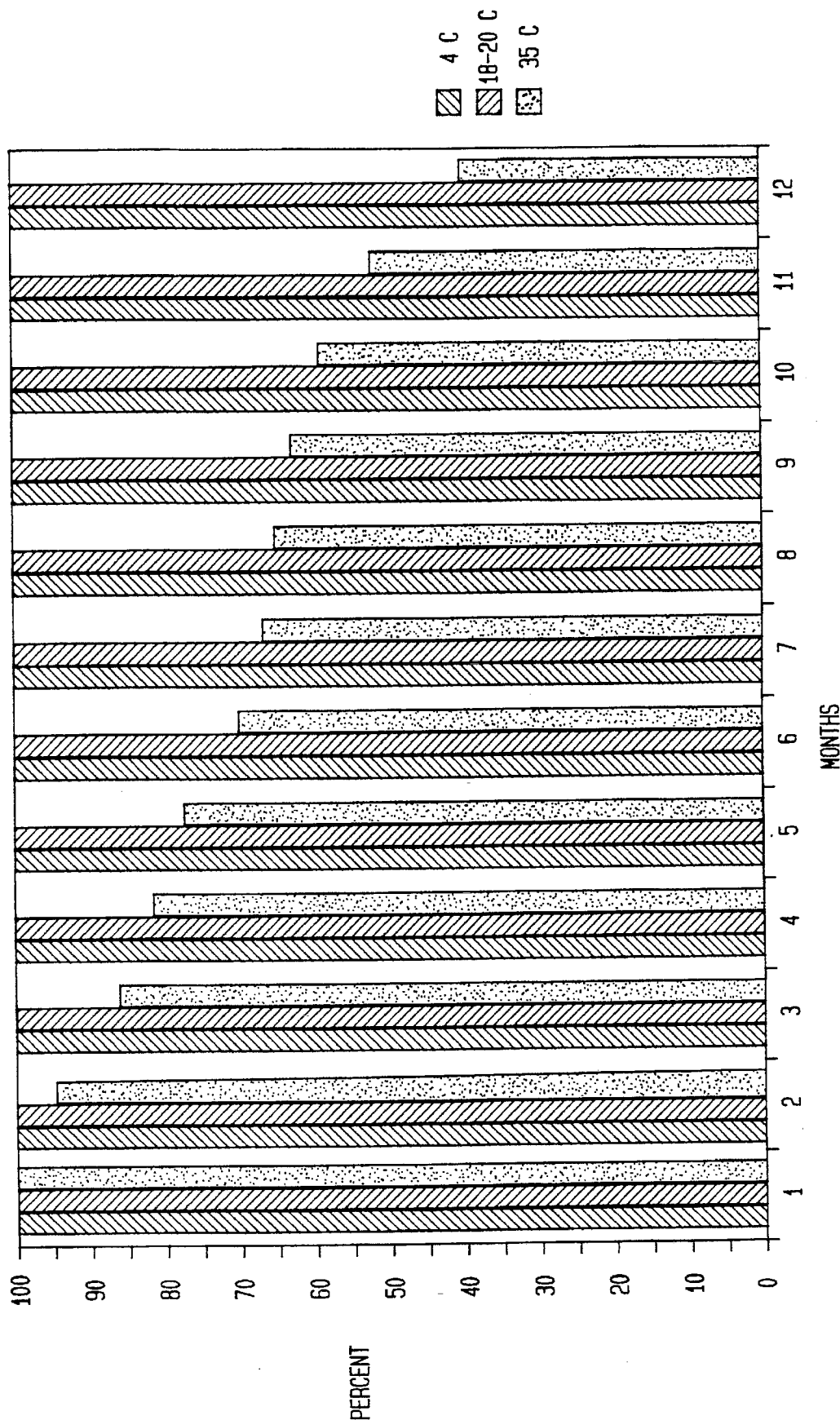

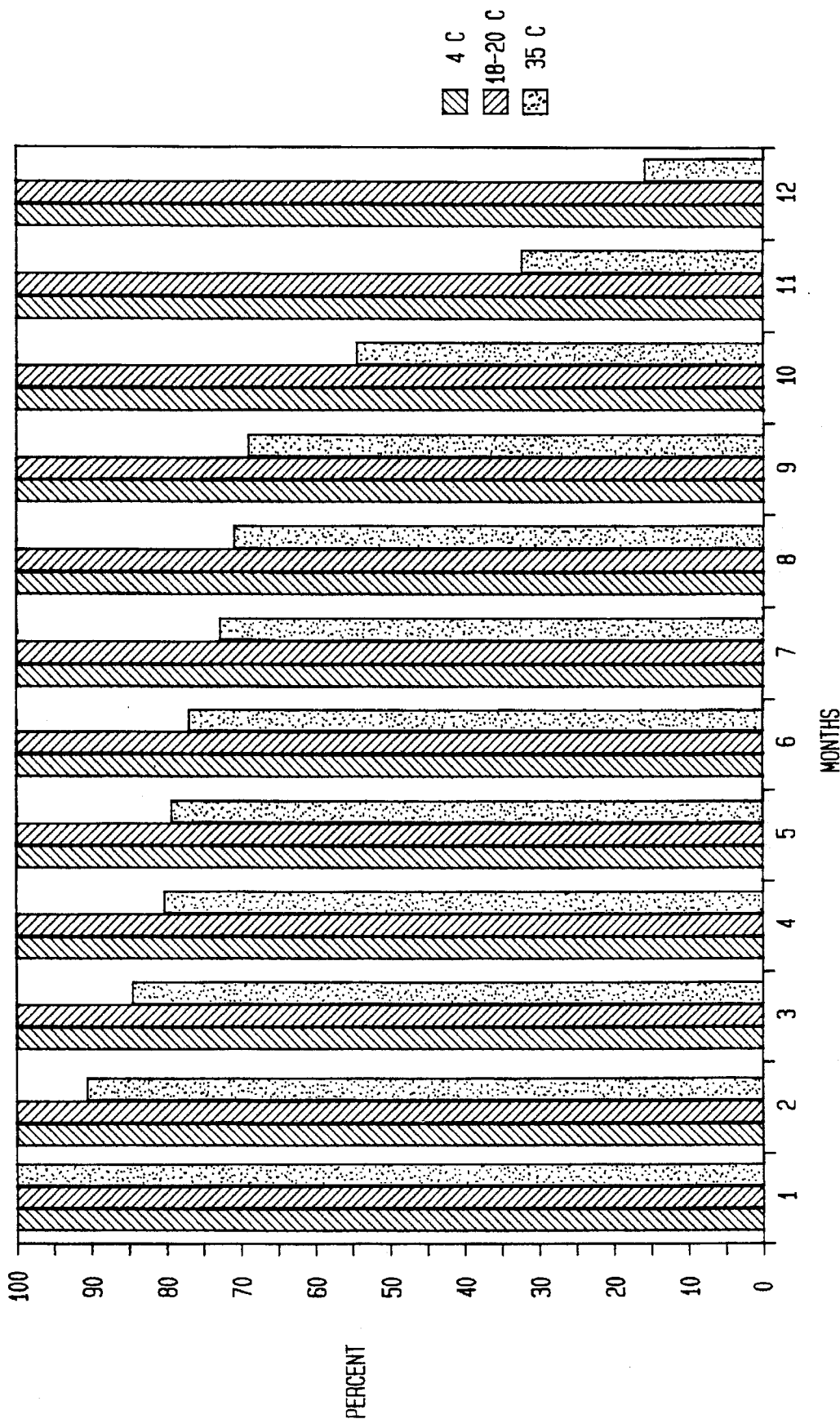

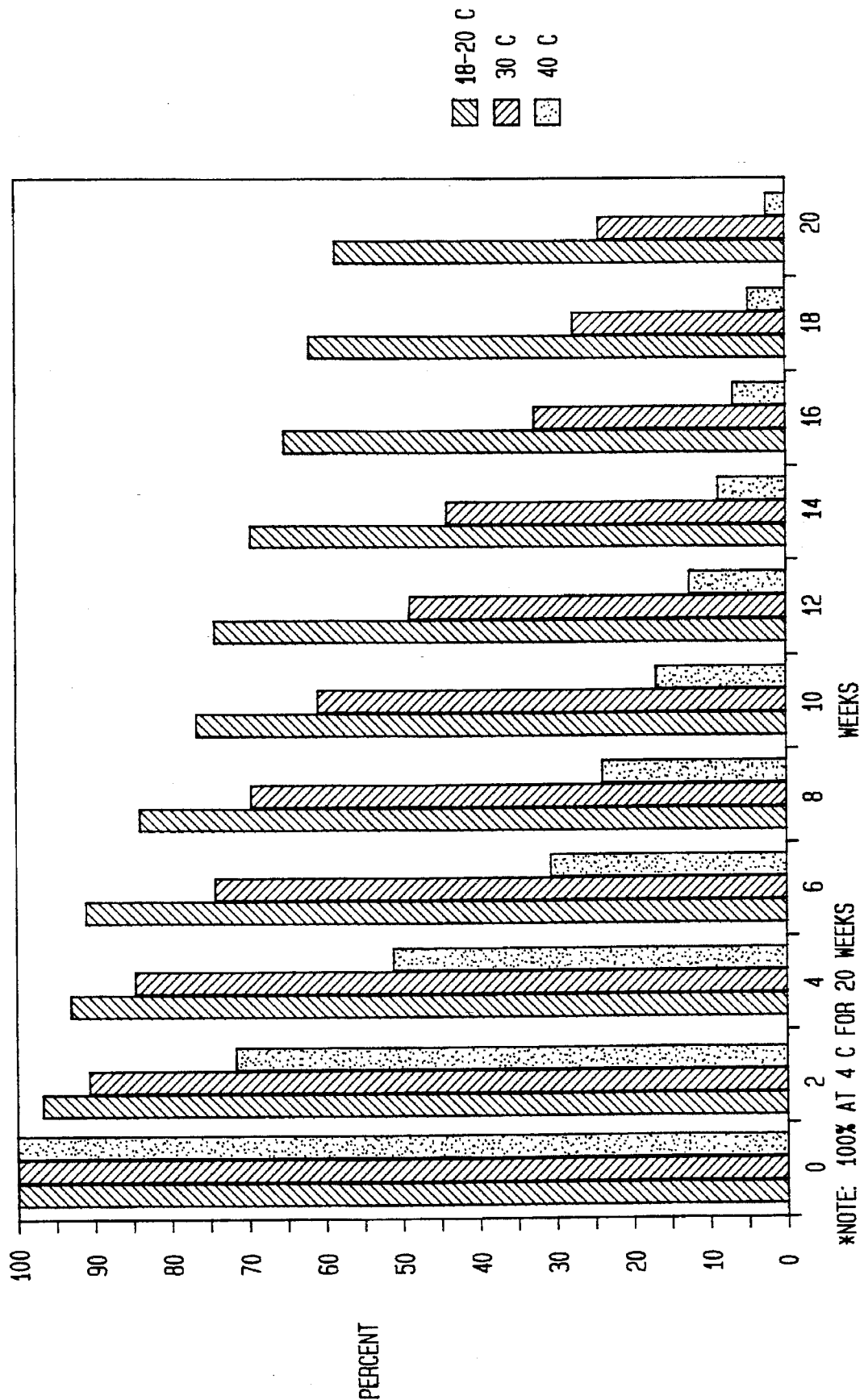

HYDROLYTIC STABILIZER FOR UNSTABLE ORGANIC IONS

This is a continuation of application Ser. No. 07/912,569 filed Jul. 13, 1992, now U.S. Pat. No. 5,238,927, which is a File Wrapper Continuation of application Ser. No. 07/621,654 filed Nov. 30, 1990 now abandoned.

This invention relates to hydrolytically unstable organic ionic compounds stabilized in aqueous solution with cyclodextrins. More particularly, the present invention relates to hydrolytically unstable cationic pyridinium oximes or aldoximes effective in the reactivation of carboxy, choline and other esterases inhibited by organophosphorus nerve toxins, made stable in aqueous solution by cyclodextrins. The present invention also relates to systems for rapidly administering the hydrolytically unstable quaternary pyridinium oxime or aldoxime reactivators of carboxy, choline and other esterases stabilized in aqueous solution by cyclodextrins.

Extensive studies for over ten years have lead to the development of quaternary pyridinium compounds, such as quaternary pyridinium oximes and aldoximes, which are effective in the treatment of nerve poisoning by organophosphorus carboxy, choline and esterase inhibitors. Such organophosphorus toxins are the active ingredient of the chemical warfare nerve agents sarin, VX, tabun and soman, and are also the active ingredient of many household, agricultural and industrial pesticides.

Quaternary pyridinium oximes and aldoximes effective in the treatment of organophosphorus toxin nerve poisoning include mono-quaternary-pyridinium oximes and aldoximes such as 2-PAM (pralidoxime, 2-hydroxyiminomethylpyridinium-1-methyl chloride), and bis-quaternary-pyridinium oximes and aldoximes such as the H- series of oximes and aldoximes. The H- series of bis-quaternary-pyridinium oximes and aldoximes includes the most effective known antidote in the treatment of organophosphorus toxin nerve poisoning, namely HI-6 (1-(2-hydroxyiminomethylpyridinium)-2-(4-carboxyamidopyridinium)-dimethyl ether dichloride).

One drawback to the use of quaternary pyridinium oximes and aldoximes in the treatment of nerve poisoning by organophosphorus toxins is that such compounds are hydrolytically unstable, but must nevertheless be administered in aqueous solution, meaning that ordinarily these materials cannot be stored for extended periods in their ready-to-use form. There is no other known solvent in which these materials are not hydrolytically unstable. This is a rather significant problem because organophosphorus toxins, whether chemical nerve agents or pesticides, are fast-acting, allowing no time for the preparation of an antidote solution. Use of these materials by the armed services as chemical nerve agent antidotes in field kits therefore requires frequent replacement of the field kits to ensure that the antidote is fresh, effective and ready for use in an emergency. The instability of these materials has also hindered their acceptance in consumer, industrial and agricultural applications.

Stabilizers for aqueous solutions of quaternary pyridinium oximes and aldoximes are known. Acetate/acetic acid pH 3.0 buffers have long been used for this purpose. U.S. Pat. No. 4,305,947 to Bartner discloses the stabilizing of aqueous solutions of 2-PAM salts with hydroxylamine salts. The problem with acetate buffer and hydroxylamine salt stabilizers for quaternary pyridinium oximes and aldoximes is that they are only effective for mono-quaternary pyridinium oxime or aldoximes and only for concentrations up to about 100 mg/ml, while the efficacy of the mono-quaternary pyridinium oximes and aldoximes ranges between about 125 and 400 mg/70 kg body weight. A stabilizer system is required for quaternary pyridinium oximes and aldoximes that will maintain the effective concentration of these materials at levels greater than 100 mg/ml.

Cyclodextrin polyethers are described in U.S. Pat. No. 3,459,731 to Gramera. This patent discloses that cyclodextrins form a variety of crystalline inclusion complexes with many organic substances, particularly with organic liquids of low solubility in water. The cyclodextrins are homologous cyclic molecules containing six or more alpha-D glucopyranose units linked together at the 1,4 positions as in amylose. The six unit cyclodextrin is known as alpha-cyclodextrin, the seven unit cyclodextrin is known as beta-cyclodextrin and the eight unit cyclodextrin is known as gamma-cyclodextrin. Being cyclic, the molecule forms a torus. The inclusion complex is formed by the insertion of the included compound in the center of the torus. The center of the cyclodextrin torus is hydrophobic, while the exterior is hydrophilic, explaining the effectiveness of this molecule in solubilizing hydrophobic materials of low water solubility. The insertion complex forms because of the affinity of the hydrophobic "guest" molecule for the hydrophobic interior of the "host" cyclodextrin, yet the complex remains water soluble because of the hydrophilic exterior of the cyclodextrin.

Cyclodextrins are also known to form inclusion complexes with hydrolytically unstable polar molecules to provide stable, aqueous solutions of the polar compounds. This is disclosed in Yonezawa, *Agric. Biol. Chem.*, 45(2), 505–506 (1981), Glomot, *Int. J. Pharm.*, 46, 49–55 (1988), Bekers, *Pharm. Week.*, 10, 207 (1988), Bekers, *Proc. Fourth Int. Sym. Cyclodextrins* (Huber and Szejtli, Eds.), 313–317 (1988), and Green, *J. Pharm. Sci.*, 78(5), 427 (1989).

SUMMARY OF THE INVENTION

It has now been discovered that cyclodextrins can be utilized to form stable inclusion complexes with hydrolytically unstable ionic compounds, including cationic compounds such as hydrolytically unstable quaternary compounds. While cyclodextrins have formed hydrolytically stable inclusion complexes with hydrolytically unstable polar molecules, from this, there would be no reason to expect that the hydrophobic interior of the cyclodextrin would accommodate a charge-bearing organic compound such as an organic anion, cation or zwitterion.

Therefore, according to one embodiment of the present invention, storage-stable, rapidly solvated organic inclusion complexes are provided of a hydrolytically unstable organic ionic compound and a cyclodextrin, which cyclodextrin is capable of forming a hydrolytically stable inclusion complex with the ionic compound. This aspect of the present invention includes storage-stable rapidly solvated organic inclusion complexes of quaternary pyridinium oximes and aldoximes, including reactivators of carboxy, choline and other esterases effective in the treatment of organophosphorus toxin nerve poisoning.

According to another embodiment of the present invention, storage-stable aqueous solutions of the organic inclusion complexes of the present invention are provided of a hydrolytically unstable organic ionic compound and a cyclodextrin, which cyclodextrin is capable of forming a hydrolytically stable inclusion complex with the solvated ion. This aspect of the present invention includes storage-stable aqueous solutions of the above-described hydrolytically unstable quaternary pyridinium oximes and aldoximes and cyclodextrins.

The present invention accordingly also includes systems for rapidly administering an aqueous solution effective in the treatment of organophosphorus toxin nerve poisoning to a mammal in need thereof. In one system according to the present invention, a storage-stable aqueous solution of an inclusion complex of a hydrolytically unstable quaternary pyridinium oxime or aldoxime compound capable of reactivating carboxy, choline and other esterases inhibited by organophosphorus toxins and a cyclodextrin capable of forming a hydrolytically stable inclusion complex with the quaternary pyridinium compound, is combined with means for rapidly administering the aqueous solution. In another system according to the present invention, a storage-stable rapidly solvated organic ionic inclusion complex of a hydrolytically unstable quaternary pyridinium oxime or aldoxime compound capable of reactivating carboxy, choline and other esterases inhibited by organophosphorus toxins with a cyclodextrin capable of forming a hydrolytically stable inclusion complex with the quaternary pyridinium compounds is combined with means for rapidly solvating and administering the inclusion complex.

While not being bound by any particular theory, it is believed that unstable organic ionic compounds such as HI-6 are subject to hydrolytic attack in the region of the charge-bearing nitrogen atom, and that formation of an inclusion complex within the "host" torus of the cyclodextrin shields the cation from attack at this point. It is further believed that formation of the cyclodextrin inclusion complex also shields the unstable polar oxime and aldoxime substituents from hydrolytic attack. Other objects, features and advantages of the compositions and systems of the present invention will be more readily apparent from the detailed description of the preferred embodiment set forth below.

BRIEF DESCRIPTION OF THE DRAWINGS

FIG. 4 is a graph depicting the concentration loss, with time, of cyclodextrin stabilized 50 mg/ml HI-6 solutions stored at 4° C., 18°–20° C. and 35° C.;

FIG. 5 is a graph depicting the concentration loss with time of 50 mg/ml HI-6 solutions without cyclodextrin stored at 4° C., 18°–20° C. and 35° C.;

FIG. 6 is a graph depicting the concentration loss with time of cyclodextrin stabilized 90 mg/ml HI-6 solutions stored at 4° C., 18°–20° C. and 35° C.; and FIG. 7 is a graph depicting the concentration loss with time of 100 mg/ml HI-6 solutions without cyclodextrin stored at 18°–20° C., 30° C. and 40° C.

DETAILED DESCRIPTION OF THE PREFERRED EMBODIMENT

Figure 1:
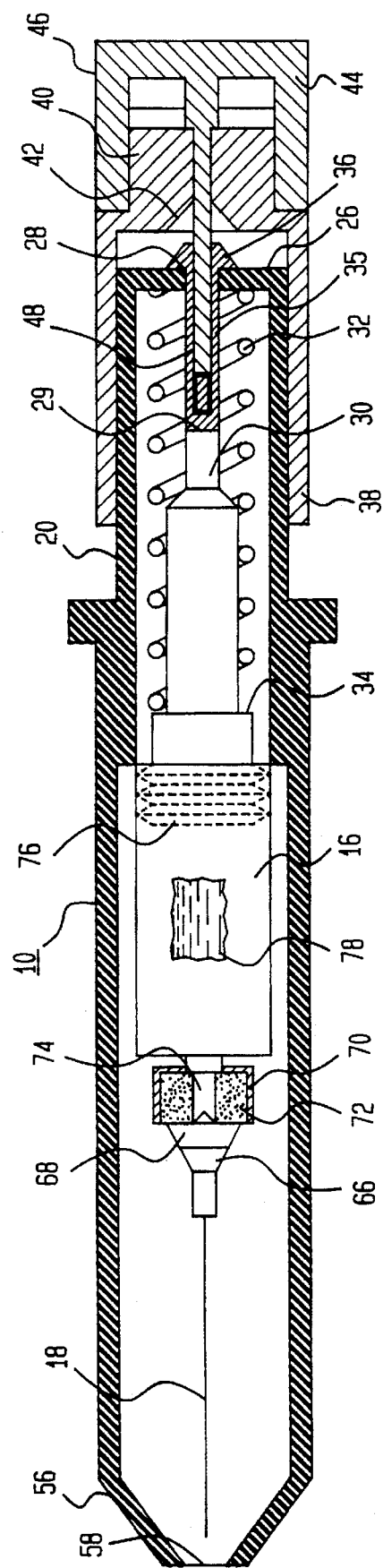
FIG. 1 is a side, cross-sectional view of an injection device for use in one system of the present invention, with the gun in cocked position and the cannula sheathed within the cartridge holder.

The present invention employs cyclodextrin compounds as stabilizers for hydrolytically unstable organic ionic compounds. Dissolving the cyclodextrin in water together with a compound that dissolves to form hydrolytically unstable organic ions results in the formation of an ion-cyclodextrin inclusion complex, the aqueous solution of which is hydrolytically stable.

Cyclodextrins suitable for use with the present invention may be alpha, beta or gamma cyclodextrins. Whether an alpha, beta or gamma cyclodextrin should be selected for complexing with the organic ionic compound to be stabilized can be readily determined by one of ordinary skill in the art without undue experimentation. The objective is the selection of a cyclodextrin having a torus of optimum cavity size to permit penetration of the guest molecule, without penetration of the aqueous solvent. A typical screening of cyclodextrins is illustrated in the above-cited Yonezawa, *Agric. Biol. Chem.*, 45(2), 505–506 (1981). The compound to be stabilized is mixed in distilled water with a candidate cyclodextrin and evaluated for the formation of cyclodextrin complexes. If the complex does not form, then the cyclodextrin torus cavity size is too small. The cyclodextrin complexes that do form are evaluated for stability in aqueous solution, with selection of the cyclodextrin providing the greatest aqueous stability. The evaluation and selection of cyclodextrin inclusion complexes disclosed in *Yonezawa* is incorporated herein by reference thereto.

The cyclodextrins are then used to form inclusion complexes, which are stable in aqueous solution, with hydrolytically unstable organic ionic compounds. The term "hydrolytically unstable organic ionic compounds" is not meant to imply that all organic ionic compounds are hydrolytically unstable. Rather, this term refers to members of the class of organic ionic compounds that are hydrolytically unstable, and excludes those members that are hydrolytically stable. By definition, this term also refers only to those hydrolytically unstable compounds in which the charge-bearing atom participates in the degradation reaction.

The hydrolytically unstable organic ionic compounds suitable for use with the present invention include anions, cations and zwitterions. Among the cations suitable for use in the present invention are mono- and bis-quaternary pyridinium compounds, particularly the oxime and aldoxime derivatives thereof.

As mentioned above, mono- and bis-quaternary pyridinium oximes and aldoximes are effective in the treatment of organophosphorus toxin nerve poisoning, but a number of these compounds are hydrolytically unstable. The hydrolytically unstable members of this species include mono-quaternary pyridinium oximes and aldoximes including 2-PAM and P2S and bis-quaternary-pyridinium oximes and aldoximes, including the H-series of compounds having the structural formula:

$$\underset{CH_2-R_3-CH_2}{\underset{|}{\overset{R_1}{\underset{N^+}{\bigcirc}}}\phantom{x}\underset{|}{\overset{R_2}{\underset{N^+}{\bigcirc}}}}$$

wherein $R_1$ is a 2- or 4-substituted oxime substituent having the formula: —CH=NOH and $R_2$ is a 3- or 4-substituent selected from the group consisting of: —CH=NOH —N(CH$_3$)$_2$, —SC$_2$H$_5$, —SCH(CH$_3$)$_2$, $$-\overset{O}{\underset{\|}{C}}-NH_2, \quad -\overset{O}{\underset{\|}{C}}-\bigcirc, \quad -\overset{O}{\underset{\|}{C}}-\bigcirc \quad \text{and}$$

$$-\overset{O}{\underset{\|}{C}}-CH(CH_3)_2$$

and $R_3$ is —O— or —$CH_2$—.

When $R_1$ is substituted in the 2-position, $R_3$ is —O— and $R_2$ is a 4-substituted amide having the formula:

$$-\overset{O}{\underset{\|}{C}}-NH_2$$

the oxime is HI-6, the most effective compound of the H-series in the reactivation of carboxy, choline and other esterases inhibited by organophosphorus nerve toxins. The preferred cyclodextrins for use with HI-6 are beta-cyclodextrins, more preferably 2-hydroxypropyl beta-cyclodextrins such as Molecusol MHPB manufactured by Pharmatec, Inc. of Alachua, Fla.

The hydrolytically unstable organic ionic compound to be stabilized and the cyclodextrin are dissolved together in water to form the inclusion complex. The water is distilled or deionized water. While the molar ratio of cyclodextrin to ionic compound is not critical, the stabilizing effect of the cyclodextrin increases as the ratio of cyclodextrin to ionic compound increases. The combination of the cyclodextrin and ionic compound to form the inclusion complex is an equilibrium reaction; therefore, an excess of cyclodextrin over the ionic compound is desirable to insure that no non-complexed ionic compound remains in solution. Accordingly, a molar ratio of cyclodextrin to ionic compound over about 1:1 is preferred, and a molar ratio over about 2:1 is even more preferred.

In addition to the materials described thus far, the compositions of the invention can be combined with other optional additives suited for use with the end-use application. For example, one or more additional non-cyclodextrin stabilizers can be added to the aqueous solution, as well as one or more preservatives and one or more additional pharmaceutical compositions effective in alleviating the symptoms of organophosphorus toxin nerve poisoning.

More specifically, one or more additional stabilizers such as acetate/acetic acid pH 3.4 buffer, hydroxylamine and the like may optionally be present in the aqueous solution at concentrations between about 5 mg/ml and about 10 mg/ml. One or more preservatives, such as hindered phenolics such as methylparaben, propylparaben, butylated hydroxytoluene, butylated hydroxyanisole and the like may optionally be present in millimolar concentrations between about 1 and about 3. One or more pharmaceutical compositions such as one or more non-pyridinium anticholinergic compounds such as benactyzine, aprophen and the like may optionally be present in millimolar concentrations between about 15 and about 50. In addition, other pharmaceutical compositions that can optionally be included in the aqueous solutions of the present invention include atropine sulfate, which may be present in millimolar concentrations between about 2 and about 6.

The techniques associated with the preparation of the storage-stable aqueous inclusion complex solution of a hydrolytically unstable organic ionic compound and a cyclodextrin in accordance with the present invention are well known and may vary somewhat depending upon the specific organic ionic compound and cyclodextrin, without departing from the essential parameters relating to dissolving an organic ionic compound and a cyclodextrin in water to form an inclusion complex. Such other details are provided for purposes of illustration and to provide a best mode for the practice of the invention, and therefore the invention should not be limited to those parameters.

The storage-stable aqueous solutions of the present invention may be prepared by dissolving a hydrolytically unstable organic ionic compound and a cyclodextrin in distilled water. Preferably, an aqueous solution of the cyclodextrin is prepared first, into which the organic ionic compound is dissolved, so as to avoid degradation of the hydrolytically unstable organic ionic compound, if it were added first, prior to the addition of the cyclodextrin. The cyclodextrin solution is prepared by dissolving a predetermined quantity of cyclodextrin in distilled water, with stirring. Distilled water at room temperature is suitable, however, it is preferable that the solution be maintained at a temperature between about 18° and about 25° C. The mixture should be stirred for at least 0.5 hours, and preferably at least 1 hour. The predetermined quantity of the hydrolytically unstable organic ionic compound is added next with stirring. Again, the solution may be maintained at room temperature or preferably at a temperature between about 18° and about 25° C., with stirring. After addition of the organic ionic compound, the mixture should be stirred for at least 0.25 hours, preferably 0.5 hours. The optional stabilizers, preservatives and pharmaceutical compositions may be added prior to, along with, or subsequent to the addition of the hydrolytically unstable organic ionic compound.

The storage-stable rapidly solvated organic ionic inclusion complex of a hydrolytically unstable organic ionic compound and a cyclodextrin in accordance with the present invention may be prepared from the storage-stable aqueous solutions of the present invention by well-known techniques that may vary somewhat depending upon the specific organic ionic compound and cyclodextrin, without departing from the essential parameters relating to lyophilization of aqueous solutions. Again, such other details are provided for purposes of illustration and to provide a best mode for the practice of the invention, and therefore, the invention should not be limited to those parameters.

The storage-stable rapidly solvated organic ionic inclusion complexes of the present invention may be prepared by fast freezing the aqueous inclusion complex of the present invention. The liquid is then removed from the frozen solution by exposing the frozen solution to a reduced temperature and pressure environment so that substantially all of the frozen liquid sublimes, leaving behind the organic ionic inclusion complex.

The storage-stable aqueous solutions of quaternary pyridinium oxime or aldoxime ionic compounds effective in the reactivation of carboxy, choline and other esterases inhibited by organophosphorus nerve toxins can be utilized in systems for rapidly administering an aqueous solution effective in the treatment of organophosphorus toxin nerve poisoning to a mammal in need thereof. Such systems combine the storage-stable aqueous solution of a hydrolytically unstable quaternary pyridinium oxime or aldoxime compound capable of reactivating carboxy, choline and other esterases inhibited by organophosphorus toxins and a cyclodextrin capable of forming a hydrolytically stable inclusion complex with the quaternary pyridinium compound, together with a means for rapidly administering the aqueous solution.

The means for rapidly administering the aqueous solution is an Auto-Injector hypodermic injection device of the gun type wherein a plunger is cocked against the force of a source of potential energy, such as a spring, which plunger, when released, will exert a force on a piston to expel the aqueous solution of the present invention from an ampoule associated with the gun. The Auto-Injector may contain a pre-mixed aqueous solution of an organic inclusion complex of a hydrolytically unstable quaternary pyridinium oxime or aldoxime compound capable of reactivating carboxy, choline and other esterases inhibited by organophosphorus toxins with a cyclodextrin. Auto-Injectors for administering aqueous solutions are essentially conventional and are described in U.S. Pat. Nos. 3,712,301 and 3,797,489 to Sarnoff, the disclosure of which are hereby incorporated herein by reference thereto.

The Auto-Injector may also be of a type containing a storage-stable rapidly solvated organic ionic inclusion complex of a hydrolytically unstable quaternary pyridinium oxime or aldoxime compound capable of reactivating carboxy, choline and other esterases inhibited by organophosphorus toxins with a cyclodextrin and having means for rapidly solvating the inclusion complex to form the aqueous solution of the present invention, effective in the treatment of organophosphorus toxin nerve poisoning for administration to a mammal in need thereof. Auto-Injectors containing materials to be solvated and having means for rapidly solvating materials are essentially conventional and are described in U.S. Pat. No. 4,226,236 to Genese and U.S. Pat. Nos. 4,689,042 and 4,755,169 to Sarnoff, the disclosures of which are hereby incorporated herein by reference thereto.

Figure 2:
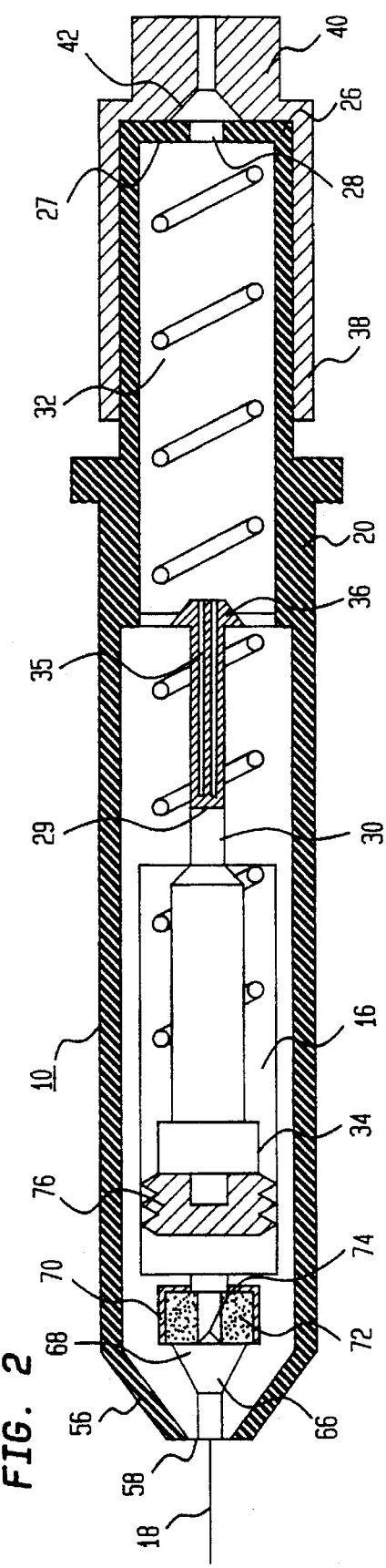
FIG. 2 is a side, cross-sectional view of the injection device of FIG. 1, with the gun released and the contents of the cartridge expelled therefrom.

A system for rapidly administering the aqueous solutions of the present invention is depicted in FIGS. 1 and 2, showing an assembly of a gun indicated generally at 10, having an inner sleeve 20 containing an ampoule 16 and cannula 18.

The inner sleeve 20 is closed at its rearward end 26 except for a central opening 28 for the passage there through of the bifurcated end 29 of plunger 30, which, in cooperation with the outer face of the end 26 of the sleeve 20 provides a restraint against the forcing of the plunger 30 toward the ampoule 16. This is accomplished by the action of spring 32, which is under compression between a shoulder 34 on plunger 30 and the inner face 27 of the rearward end 26 of inner sleeve 20. The end 29 of plunger 30 has bifurcations 35, and the plunger 30 is normally positioned so that the conical tips 36 of the bifurcations 35 have flat faces resting against the outer face of end 26.

When the bifurcations are compressed together, the conical portions 36 are of a diameter less than the diameter of opening 28 and the spring is then free to expand and rapidly move the plunger to the ampoule. An outer sleeve 38 is telescopically movable on the inner sleeve 20, and is provided with a thickened end 40 having an inner central cam face 42 adapted to engage the conical portions 36 and squeeze them together when the outer sleeve is moved towards the ampoule. To prevent inadvertent release of the plunger 30, a safety device 44 is provided, comprising a knurled manually engagable cap 46 having an integral pin 48 insertable between the bifurcations so as to prevent collapsing movement of the conical portions 36.

The opposite end of inner sleeve 20 has a conical nose 56 with a central opening 58. Cannula 18 is attached to ampoule 16 by hollow cap 68 firmly embracing a sleeve 66 fixed to the cannula 18 and spun over the flange 70 at the neck portion of the ampoule. Within the ampoule, a resilient diaphragm 72 is held to the flange 70 by the cap 68. The diaphragm 72 is adapted to be burst by application of fluid pressure to a thinned wall 74 thereof. Within the ampoule at the end opposite the cannula is a piston 76 forming a space between it and the diaphragm 72 for the aqueous solution 78 of the present invention. When the aqueous solution 78 is forced toward the cannula by operation of piston 76, the fluid pressure will invert the V-shaped wall 74 and stretch it so that it eventually bursts.

In the use of the injector device, first the gun 10 is cocked by forcing the bifurcations 35 of the plunger 30 into the end of the inner sleeve 20 until the conical portions 36 pass through the opening 28 and spread out to engage the outer surface of the end 26 of inner sleeve 20. For safety reasons, the pin 48 is inserted between the bifurcations of the plunger. To use the device, the safety pin 48 is removed and the conical nose 56 of the inner sleeve 20 is pressed firmly against the desired area of injection. Upon telescopic action of sleeve 38 on sleeve 20, conical portions 36 pass through opening 28 and the plunger 30 is released. Under the action of spring 32, the plunger shifts the ampoule so that the canuula passes through the opening 58 and enters the flesh of the patient. Movement of the ampoule continues until arrested by conical nose 56. Continued movement of the plunger and movement of the piston 76 in the ampoule causes an expulsion of the aqueous solution through the cannula into the patient.

Figure 3:
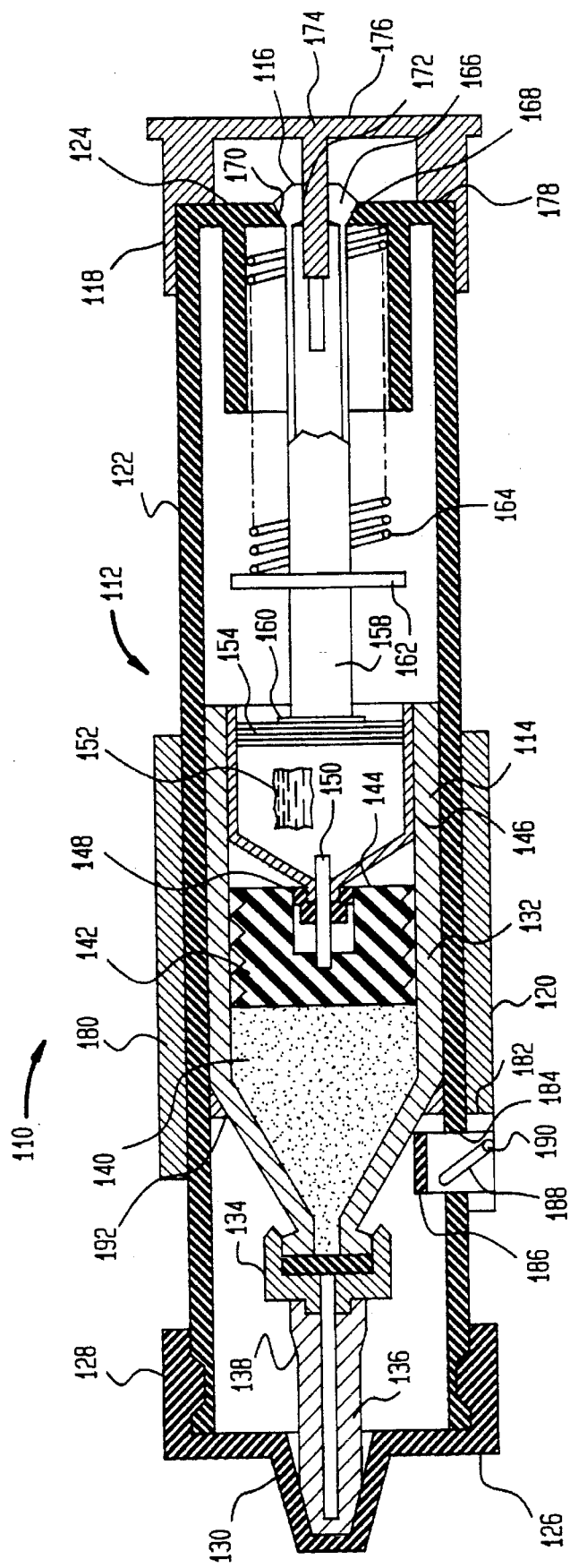
FIG. 3 is a side, cross-sectional view of an injection device for use in another system of the present invention, showing the parts in their storage position.

A system for rapidly solvating and administering the storage-stable inclusion complexes of the present invention is depicted in FIG. 3, showing an assembly of a gun indicated generally at 110, having an outer housing assembly 112 within which is mounted a dual container cartridge assembly 114 and a stressed spring assembly 116. The apparatus 110 also includes a safety cap and releasing pin assembly 118 which is operable in response to a first predetermined manual actuating procedure to effect a first release of the stress spring assembly 116 for effecting the solvating function and a second releasing assembly 120 operable in response to a second predetermined manual actuating procedure to effect a second release of the stressed spring assembly 116 for effecting the injecting function.

The outer housing assembly 112 includes a tubular housing member 122 in the form of a cylinder having an open forward end and a rearward end closed by an end wall 124 having a central opening therein. The housing assembly 112 also includes a forward housing member 126 which includes a rearwardly extending skirt 128 having a snap connection over the exterior periphery of the forward end of the tubular frame member 122 and a central forwardly extending nose portion 130 which is centrally apertured.

A dual container cartridge assembly 114 includes an outer container 132 which is in the form of a cylindrical container open at its rearward end and having a necked down exteriorly flanged forward end. A hub assembly 134 served to connect the rear end of a hypodermic needle 136 in communicating relation with the forward necked down end of the container 132. A resilient sheet 138 is fixed over the hypodermic needle 136 and its tip serves to sealingly retain liquid within the hypodermic needle 136 while in its storage condition and to retain the hypodermic needle in a sterile condition.

Mounted in the forward end of the outer container 132 is the storage-stable rapidly solvated organic ionic inclusion complex of the present invention 140, preferably in the form of dry powder. The inclusion complex 140 is confined at its rearward end by a large piston 142 which is a deep recess 144 formed in the rear end portion thereof so as to define a thin forward central portion in the piston 142. Mounted within the outer container 132 rearwardly of the piston 142 is an inner container 146 which is at a configuration similar to the configuration of the container 132 but of smaller diameter. The necked down exteriorly flanged forward end portion of the inner container 146 is connected, as by a hub assembly 148 to a short needle-like element 150, the sharpened end of which is embedded within the central thin wall portion of the piston 142 so as to provide a liquid seal thereof. Mounted within the inner container 146 is aqueous solvent 152 which is confined at its rear end by a piston 154 of resilient material.

The stressed spring assembly 116 includes an elongated plunger 158 having a flanged forward end 160 arranged to be disposed in engagement with the piston 154 and an intermediate flange 162 for reseating one end of a stressed coil spring 164, the opposite end of which engages the rear wall 124 of the outer tubular housing member 122. The rear end portion of the plunger 158 is slotted to form a plurality of spring fingers 166 which have plunger retaining surfaces 168 arranged to be engaged with a frustoconical plunger retaining surface 170 in the end wall 124 and interior plunger releasing surfaces 172 which engage the exterior of a releasing pin 174 forming a part of the assembly 118. The assembly 118 includes a safety cap 176 which is in the form of an end wall having a forwardly extending skirt. The pin 174 is integral with the central forward surface of the cap and wall and the skirt is recessed to engage over the exterior periphery of the rear end of the tubular housing member 122 and to provide a shoulder 178 to limit the forward movement of the cap 176 by engagement with the rear end wall 124.

The second releasing assembly 120 includes a manually engageable sleeve 180 slidably frictionally mounted over the exterior periphery of the outer housing member 122. Formed in the forward end of the sleeve 180 is a slot 182 which registers with a smaller slot 184 formed in the peripheral wall of the tubular housing member 122. A releasing lock or bolt 186 is slidably mounted in the slots 182 and 184 and has an angular slot 188 formed therein within which a pin 190 extends. Pin 190 is fixed to the portion of the sleeve 180 defining slot 182. The bolt 186 in its locking or storage position extends into the interior of the housing member 122 and engages in front of an annular fitment 192 mounted forwardly of the outer container 146 at the position where it begins to neck down.

In operation, when it is desired to utilize the apparatus 110, the operator first removes the safety cap 176 which has the effect of withdrawing releasing pin 174. The angular relationship between the plunger retaining surfaces 168 and 170 and the strength of spring 164 is such that movement of the plunger 158 commences in response to the withdrawal of the releasing pin 174. As soon as releasing pin 174 is no longer in engagement with the plunger releasing surfaces 172, the spring fingers 166 of the plunger 158 are cammed radially inwardly so as to allow the plunger 158 to move forwardly. The forward movement of the plunger is transmitted through the forward end 160 the piston 154 which, in turn, is transmitted through the aqueous solution 152 to the inner container 146. Consequently, during the initial movement of the plunger 158 following the first predetermined manual actuating procedure of removing the safety cap 176, the inner container 140 sticks together with its hub assembly 148 and needle 150 is moved forwardly. On the other hand, forward movement of the piston 142 is resisted by virtue of the presence of the organic inclusion complex powder 140 forwardly thereof and consequently the needle element 150 is pierced through the thin central portion of the piston 142 so as to communicate the interior of the inner container 146 with the interior of the outer container 132. As soon as this communication takes place, the piston 142 and inner container member 146 are moved rearwardly as the aqueous solution 152 flows from the inner container into the outer container. Because the pressure area of the piston 142 is greater than the pressure area of the piston 154, the flow of liquid from the inner container 146 into the outer container 132 will continue until such time as the piston 154 reaches the forward end of the inner container 146. Spring 164 has expanded actually only a small amount and, hence, considerable stress remains in the coil spring. This stress imposes a force upon the plunger 158 through the flange 162 which is transmitted through the piston 154, container 146, piston 142 and forwardly thereof to the outer container 132. The container 132 is prevented from moving forwardly under the bias of the initially released spring 164 through the engagement of the locking bolt 186 with the fitment 192.

The organic inclusion complex 140 then dissolves in the aqueous solution 152 to form the aqueous solution of the organic inclusion complex of the present invention. Injection is accomplished by the operator gripping the outer periphery of the sleeve 180 and moving the nose portion 130 into engagement with the skin of the patient in the area where the injection is to take place as, for example, the thigh. As the operator applies a forward force to the exterior of the sleeve 180, the pin 190 carried thereby is moved forwardly with respect to the outer housing member 122. This forward movement of the pin 190 by virtue of its engagement within the angular slot 188 causes the locking bolt 186 to move radially outwardly through the slots 184 and 182 into a position disposed out of engagement with the fitment 192. This movement then constitutes the second predetermined manual actuating procedure which effects a second release of the stressed spring 164. This force which previously was acting upon the outer container 132 to move the same forward now causes this actions to take place and the needle 136 moves outwardly of the resilient sheath 138 into the muscle tissue of the patient compressing the sheath until its compression retards or stops the forward movement of the outer container 132. Further movement under the bias of spring 164 results in the forward movement of the piston 142 within the outer container 132 until the piston reaches the forward end of the container discharging the last of the aqueous solution of the organic ionic inclusion complex through the needle and into the muscle tissue of the patient.

It will accordingly be appreciated that, in accordance with this invention, hydrolytically unstable organic ionic compounds may be stabilized in aqueous solution by dissolving a cyclodextrin in the aqueous solvent. The present invention is illustrated by the following example, which is not intended to limit the same.

EXAMPLE

A beta-cyclodextrin solution having a concentration of 450 mg/ml is prepared by dissolving 1.125 g of beta-cyclodextrin to a volume of 2.5 ml of distilled water. The beta-cyclodextrin is Molecusol MHPB, a 2-hydroxypropyl beta-cyclodextrin obtained from Pharmatec, Inc., Alachua, Fla.

A 50 mg/ml solution of cyclodextrin stabilized HI-6 dichloride is prepared by adding 60 mg HI-6 dichloride to 1.2 ml of the cyclodextrin solution prepared above. The HI-6 dichloride is obtained from Schweizerhall of South Plainfield, N.J. The cyclodextrin solution is maintained at 18°–20° C. while the HI-6 dissolved. The mixture is stirred for 0.5 hours and allowed to cool to room temperature with an additional 0.5 hours of stirring. A 90 mg/ml cyclodextrin-stabilized HI-6 solution is prepared in the same manner using 108 mg of HI-6 and 1.2 ml of the cyclodextrin solution.

Control aqueous solutions of HI-6 dissolved in distilled water without cyclodextrin are also prepared in the same manner. A 50 mg/ml H-6 control solution is prepared by dissolving 60 mg of HI-6 in 1.2 ml of distilled water, and a 100 mg/ml HI-6 control solution is prepared by dissolving 120 mg of HI-6 in 1.2 ml of distilled water.

The four HI-6 stock solutions are stored at 4° C., room temperature (18°–20° C.) and 35° C. for one year. Aliquot samples of 100 micro-liters are removed monthly for stability testing. This stability testing is performed by first obtaining a HPLC profile of fresh samples of each of the four HI-6 stock solutions using a prepacked 30 cm×3.9 ml I.D. micro-Bondapak $C_{18}$ column (Waters Associates, Milford, Mass., USA) with a Waters Associate's Model ALC/GPC-204 liquid chromatograph, equipped with two Model 6000 A high pressure pumps, a Model 660 solvent programmer, U6K loop injector, a Model 440 detector, set at 254 nm, a Houston Instrument Omni-Scribe A 5000 dual-pen recorder and a Columbia Scientifics supergrator-3A-integrator. The mobile phase is 0.01M 1-heptane-sulfonic acid combined with acetonitrile. A pH 3.4 acetonitrile-PIC-B7 reagent mixture with a percent ratio of 20:80 is used in an isocratic mode to separate HI-6 in the sample formulations. The multi-component samples are chromatographed using a 50:50 solvent system. Flow rates for the separations are 1.5 ml/min with column pressure ranging between 72 and 92 bar. All separations are performed at ambient temperature with samples introduced into the column through a continuous-flow loop injector. Detection limits for the method are 1 ng on-column with peak areas measured by an on-line computing integrator.

The stability of the stored samples is tested monthly in the same manner, with the chromatographs compared to the correct profile of each stock solution to determine the percentage of non-degraded HI-6 remaining. The results are presented in FIGS. 4–7.

At 50 mg/ml HI-6 concentration, no appreciable difference is seen in the control and cyclodextrin-stabilized samples at 4° C., room temperature and 35° C. However, the improvement in HI-6 stability at 90 mg/ml concentration using cyclodextrin over the 100 mg/ml control sample is evident. The 100 mg/ml control samples are aged to the 4° C. room temperature, 30° C. and 40° C. No degradation is seen in the control after 20 weeks at 4° C. However, the testing is discontinued because the room temperature sample has degraded to a level of less than 65% non-degraded HI-6, while after 20 weeks, the room temperature cyclodextrin-stabilized HI-6 sample remains essentially non-degraded. After 12 months, this sample still contains greater than 80% non-degraded HI-6.

The results are more dramatic with elevated temperature storage. After 20 weeks, the HI-6 control sample stored at 30° C. contains less than 25% non-degraded HI-6 and the sample stored at 40° C. contains less than 5% non-degraded HI-6. The cyclodextrin stabilized HI-6 sample stored at 35° C. contains greater than 80% non-degraded HI-6 after 20 weeks.

This establishes that HI-6 stabilized with beta-cyclodextrin can be stored in ready-to-use form for extended time periods without refrigeration.

The foregoing description of the preferred embodiment should be taken as illustrating, rather than as limiting the present invention as defined by the claims. The most variations and combinations of the features described above can be utilized without departing from the present invention.

We claim:

1. A storage-stable aqueous solution comprising an inclusion complex consisting essentially of a hydrolytically unstable water-soluble bis-quaternary pyridinium oxime with a cyclodextrin selected from the group consisting of alpha-cyclodextrins, beta-cyclodextrins and gamma-cyclodextrins, which cyclodextrin is capable of forming a hydrolytically stable inclusion complex with said bis-quaternary pyridinium oxime.

2. The aqueous solution of claim 1, wherein said bis-quaternary pyridinium oxime is represented by the structural formula:

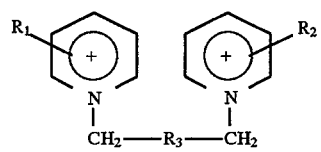

wherein $R_1$ is a two- or four-substituted oxime having the formula —CH=NOH, and $R_2$ is a three- or four-substituent selected from the group consisting of —CH=NOH, —N(CH$_3$)$_2$, —SC$_2$H$_5$, —SCH(CH$_3$)$_2$,

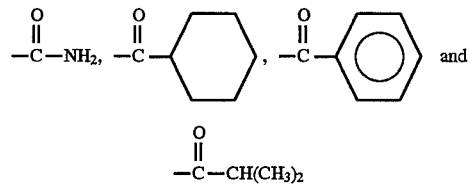

and $R_3$ is —O— or —OCH$_2$—.

3. The aqueous solution of claim 2, wherein said bis-quaternary pyridinium oxime is 1-(2-hydroxyiminomethylpyridinium)-2-(4-carboxyamidopyridinium)-dimethylether dichloride.

4. The aqueous solution of claim 3, wherein said cyclodextrin is a beta-cyclodextrin.

5. The aqueous solution of claim 1, wherein said cyclodextrin is a beta-cyclodextrin.

6. The aqueous solution of claim 5, wherein said beta-cyclodextrin is a 2-hydroxypropyl-beta-cyclodextrin.

7. The aqueous solution of claim 5, wherein said solution comprises a molar excess of cyclodextrin.

8. The aqueous solution of claim 7, wherein the molar ratio of cyclodextrin to said bis-quaternary pyridinium oxime in said solution is above about 2:1.

9. The aqueous solution of claim 1, wherein said solution further comprises one or more additives selected from the group consisting of non-cyclodextrin stabilizers, preservatives and pharmaceutical compositions.

10. The aqueous solution of claim 9, wherein said non-cyclodextrin stabilizers are selected from the group consisting of acetate/acetic acid pH 3.0 buffer and hydroxylamine.

11. The aqueous solution of claim 9, wherein said preservatives are selected from the group consisting of hindered phenolic compounds.

12. The aqueous solution of claim 11, wherein said hindered phenolic compounds are selected from the group consisting of methylparaben, propylparaben, butylated hydroxytoluene and butylated hydroxyanisole.

13. The aqueous solution of claim 9, wherein said pharmaceutical compositions are non-pyridinium anticholinergic compounds selected from the group consisting of benactyzine and aprophen.

14. The aqueous solution of claim 9, wherein said pharmaceutical composition is atropine sulfate.

15. A storage-stable rapidly solvated inclusion complex consisting essentially of a hydrolytically unstable water-soluble bis-quaternary pyridinium oxime and a cyclodextrin selected from the group consisting of alpha-cyclodextrins, beta-cyclodextrins and gamma-cyclodextrins, which cyclodextrin is capable of forming a hydrolytically-stable inclusion complex with said bis-quaternary pyridinium oxime.

16. The inclusion complex of claim 15, wherein said bis-quaternary pyridinium oxime is represented by the structural formula:

$$R_1 \text{-pyridinium}^+ - N - CH_2 - R_3 - CH_2 - N - \text{pyridinium}^+ - R_2$$

wherein $R_1$ is a two- or four-substituted oxime having the formula —CH=NOH, and $R_2$ is a three- or four-substituent selected from the group consisting of —CH=NOH, —N(CH$_3$)$_2$, —SC$_2$H$_5$, —SCH(CH$_3$)$_2$, $$-\overset{O}{\underset{\|}{C}}-NH_2,\ -\overset{O}{\underset{\|}{C}}-\text{cyclohexyl},\ -\overset{O}{\underset{\|}{C}}-\text{phenyl}\ \text{and}$$

$$-\overset{O}{\underset{\|}{C}}-CH(CH_3)_2$$

and $R_3$ is —O— or —CH$_2$—.

17. The inclusion complex of claim 16, wherein said bis-quaternary pyridinium oxime is 1-(2-hydroxyiminomethylpyridinium)-2-(4-carboxyamidopyridinium)-dimethylether dichloride.

18. The inclusion complex of claim 17, wherein said cyclodextrin is a beta-cyclodextrin.

19. The inclusion complex of claim 16, wherein said cyclodextrin is a beta-cyclodextrin.

20. The inclusion complex of claim 19, wherein said beta-cyclodextrin is a 2-hydroxypropyl-beta-cyclodextrin.

21. A system for rapidly administering an aqueous solution effective in the treatment of organophosphorus toxin poisoning to a mammal in need thereof, comprising:

a storage-stable aqueous solution comprising an inclusion complex consisting essentially of a hydrolytically unstable bis-quaternary pyridinium oxime compound capable of reactivating esterases inhibited by said organophosphorous toxins and a cyclodextrin selected from the group consisting of alpha-cyclodextrins, beta-cyclodextrins and gamma-cyclodextrins, which cyclodextrin is capable of forming a hydrolytically stable inclusion complex with said bis-quaternary pyridinium oxime compound; and means for rapidly administering said aqueous solution.

22. The system of claim 21, wherein said means for rapidly administering said aqueous solution is an auto-injector hypodermic injection device.

23. The system of claim 21, wherein said bis-quaternary pyridinium oxime is represented by the structural formula:

$$R_1 \text{-pyridinium}^+ - N - CH_2 - R_3 - CH_2 - N - \text{pyridinium}^+ - R_2$$

wherein $R_1$ is a two- or four-substituted oxime having the formula —CH=NOH, and $R_2$ is a three- or four-substituent selected from the group consisting of —CH=NOH, —N(CH$_3$)$_2$, —SC$_2$H$_5$, —SCH(CH$_3$)$_2$, $$-\overset{O}{\underset{\|}{C}}-NH_2,\ -\overset{O}{\underset{\|}{C}}-\text{cyclohexyl},\ -\overset{O}{\underset{\|}{C}}-\text{phenyl}\ \text{and}$$

$$-\overset{O}{\underset{\|}{C}}-CH(CH_3)_2$$

and $R_3$ is —O— or —CH$_2$—.

24. The system of claim 23, wherein said bis-quaternary pyridinium oxime is 1-(2-hydroxyiminomethylpyri-dinium)-2-(4-carboxyamidopyridinium)-dimethylether dichloride.

25. The system of claim 24, wherein said cyclodextrin is a beta-cyclodextrin.

26. The system of claim 21, wherein said cyclodextrin is a beta-cyclodextrin.

27. The system of claim 26, wherein said beta-cyclodextrin is a 2-hydroxypropyl-beta-cyclodextrin.

28. The system of claim 26, wherein said solution comprises a molar excess of said cyclodextrin.

29. The system of claim 28, wherein the molar ratio of said cyclodextrin to said bis-quaternary pyridinium oxime in said solution is above about 2:1.

30. The system of claim 21, wherein said solution further comprises one or more additives selected from the group consisting of non-cyclodextrin stabilizers, preservatives and pharmaceutical compositions.

31. A system for rapidly administering an aqueous solution effective in the treatment of organophosphorus toxin nerve poisoning to a mammal in need thereof, comprising:

a storage-stable rapidly solvated inclusion complex consisting essentially of a hydrolytically unstable water-soluble bis-quaternary pyridinium oxime capable of reactivating esterases inhibited by said organophosphorus toxins and a cyclodextrin selected from the group consisting of alpha-cyclodextrins, beta-cyclodextrins and gamma-cyclodextrins, which cyclodextrin is capable of forming a hydrolytically stable inclusion complex with said bis-quaternary pyridinium oxime; and means for rapidly solvating and administering said inclusion complex.

32. The system of claim 31, wherein said means for rapidly solvating and administering said aqueous solution is an auto-injector hypodermic injection device.

33. The system of claim 31, wherein said bis-quaternary pyridinium oxime is represented by the structural formula:

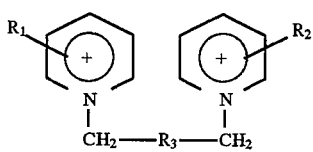

wherein $R_1$ is a two- or four-substituted oxime having the formula —CH=NOH, and $R_2$ is a three- or four-substituent selected from the group consisting of —CH=NOH, —N(CH$_3$)$_2$, —SC$_2$H$_5$, —SCH(CH$_3$)$_2$,

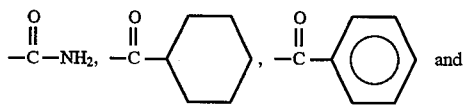

-continued $$-\overset{O}{\underset{\|}{C}}-CH(CH_3)_2$$

and $R_3$ is —O— or —CH$_2$—.

34. The system of claim 33, wherein said bis-quaternary pyridinium oxime is 1-(2-hydroxyiminomethylpyri-dinium) -2-(4-carboxyamidopyridinium)-dimethylether dichloride.

35. The system of claim 34, wherein said cyclodextrin is a beta-cyclodextrin.

36. The system of claim 31, wherein said cyclodextrin is a beta-cyclodextrin.

37. The system of claim 36, wherein said beta-cyclodextrin is a 2-hydroxypropyl beta-cyclodextrin.

* * * * *

UNITED STATES PATENT AND TRADEMARK OFFICE
CERTIFICATE OF CORRECTION

PATENT NO. : 5,629,299
DATED : May 13, 1997
INVENTOR(S) : Brown et al.

It is certified that error appears in the above-identified patent and that said Letters Patent is hereby corrected as shown below:

Column 12, line 33, the last line of claim 2, "—$OCH_2$—" should read -- -$CH_2$- --.

Signed and Sealed this

Fifteenth Day of July, 1997

BRUCE LEHMAN

*Attest:*

*Attesting Officer*      Commissioner of Patents and Trademarks